United States Patent [19]

Quadro

[11] 4,305,940
[45] Dec. 15, 1981

[54] BENZAMIDES WITH LOCAL ANAESTHETIC AND ANTIARRHYTHMIC ACTIVITY, SALTS, AND METHOD OF PREPARATION THEREOF AND PHARMACEUTICAL COMPOSITIONS THEREFROM

[75] Inventor: Giuseppe Quadro, Milan, Italy

[73] Assignee: B.B.R. Boehringer Biochemia Robin S.p.A., Milan, Italy

[21] Appl. No.: 207,902

[22] Filed: Nov. 18, 1980

[30] Foreign Application Priority Data

Dec. 7, 1979 [IT] Italy .................. 27919 A/79

[51] Int. Cl.³ .................. A61K 31/535; C07D 265/30; C07D 211/32; C07D 207/04
[52] U.S. Cl. .................. 424/248.54; 424/267; 424/274; 424/324; 424/310; 544/165; 546/234; 260/326.41; 564/168; 560/37
[58] Field of Search .................. 424/248.54, 267, 274, 424/324, 310; 544/165; 546/234; 260/326.41; 564/168; 560/37

[56] References Cited

U.S. PATENT DOCUMENTS

| | | | |
|---|---|---|---|
| 2,150,190 | 3/1940 | Rossander et al. | 564/168 |
| 2,870,146 | 1/1959 | Perron | 260/326.41 |
| 3,433,833 | 3/1969 | Satzinger et al. | 564/168 |
| 3,950,393 | 4/1976 | Keck et al. | 260/326.41 |
| 3,988,371 | 10/1976 | Hansl | 260/326.41 |
| 4,097,481 | 6/1978 | Banitt et al. | 546/234 |
| 4,158,063 | 6/1979 | Hitzel et al. | 564/168 |

Primary Examiner—Henry R. Jiles
Assistant Examiner—Jane T. Fan
Attorney, Agent, or Firm—Bucknam and Archer

[57] ABSTRACT

Benzamides of formula I

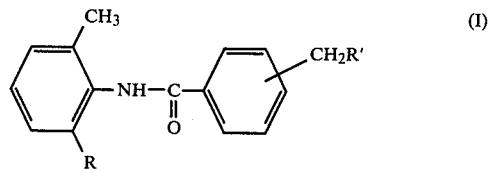

are described, in which $R=CH_3$, Cl or $COOCH_3$; R' is a member selected from the group of dialkylamine, pyrrolidine, piperidine, and morpholine radicals. $CH_2R'$ is in position ortho, meta, or para with respect to the carbonyl group; and their salts thereof with pharmaceutically acceptable acids are described. The novel compounds exhibit local anaesthetic and antiarrhythmic activity.

16 Claims, No Drawings

BENZAMIDES WITH LOCAL ANAESTHETIC AND ANTIARRHYTHMIC ACTIVITY, SALTS, AND METHOD OF PREPARATION THEREOF AND PHARMACEUTICAL COMPOSITIONS THEREFROM

The present invention relates to benzamides and more specifically to compounds of formula I:

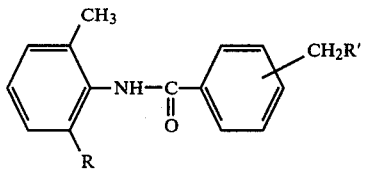

which carry a basic group. In the formula I hereinabove,

R=$CH_3$, Cl or $COOCH_3$;

$R^1$ is a dialkylamine, pyrrolidine, piperidine, or morpholine residue;

$CH_2$—$R^1$ may be in position ortho, meta, or para with respect to the carbonyl group; and Salts thereof with pharmaceutically acceptable acids.

The compounds of formula I exhibit local anaesthetic properties so that they are useful for topical application, filtration, conduction, regional block, etc., and also agents against fibrillation.

The invention also relates to pharmaceutical compositions having a local anaesthetic activity or antiarrhythmic activity which contain as the active ingredient at least one compound of formula I or its salts with pharmaceutically acceptable acids.

The invention also relates to a method of preparation for the benzamides of formula I which consists of reacting under conditions well-known in the art, a compound of formula II:

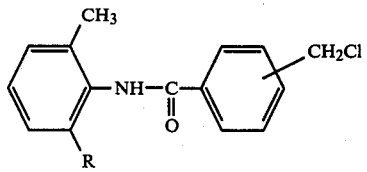

in which R has the meaning indicated hereinabove with an amine of formula III:

R'H in which R' has the same meaning defined hereinabove. According to an alternative procedure, the amides of formula I may be prepared from a derivative of benzoic acid which already contains the basic group and which also contains a chemically active substituent, of formula IV:

in which R' has the same meaning defined hereinabove and X is chlorine or alkoxy or carbethoxycarbonyloxy or another active residue by reaction under conditions well-known in the art with an aniline of formula V:

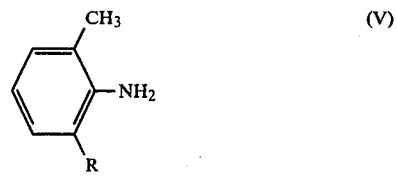

in which R has the meaning defined hereinabove.

The examples below illustrate the process according to the present invention.

EXAMPLE 1

(a) 2,6-Dimethylanilide of 4-chloromethylbenzoic acid

A solution of 18.9 g of 4-chloromethylbenzoyl chloride in 200 cc of acetone is treated with 12.1 g of m-xylidine and 30 g of anhydrous $K_2CO_3$. The mixture is heated at reflux for two hours. After cooling, the reaction mixture is filtered, the solvent is distilled off and the residue is recrystallized from ethanol.

Yield: 16.2 grams;

Melting Point: 160°–163° C.

Analysis, Calculated for: $C_{16}H_{16}ClNO$: Found: C 70.09; H 5.75; Cl 12.75; N 5.21; Calcd: C 70.18; H 5.89; Cl 12.96; N 5.12.

Application of an analogous method has provided the following intermediates:

2,6-dimethylanilide of 2-chloromethylbenzoic acid, Melting Point: 170°–172° C. (from ethanol);

2,6-dimethylanilide of 3-chloromethylbenzoic acid, Melting Point: 130°–132° C. (from ligroin);

2-methyl-6-chloroanilide of 2-chloromethylbenzoic acid,

Melting Point: 142°–144° C. (from ethanol);

2-methyl-6-carbomethoxyanilide of 2-chloromethylbenzoic acid,

Melting Point: 122°–125° C. (from ethanol);

(b) 2,6-Dimethylanilide of 4-piperidinomethyl-benzoic acid

A solution of 2.7 grams of 2,6-dimethyl-p-chloromethylbenzanilide in 200 cc of benzene is treated with a slight excess of piperidine and the mixture is heated under reflux for 4–5 hours. The mixture is cooled. The benzene phase is washed with water, then is concentrated to dryness and the residue recrystallized from ligroin. Yield: 2.1 grams; Melting Point: 176°–177° C.

Analysis: Calculated for: $C_{21}H_{26}N_2O$: Found: C 78.82; H 8.25; N 8.39; Calcd: C 78.81; H 8.13; N 8.69;

Hydrochloride, white crystalline solid, Melting Point: 270°–272° C.

EXAMPLE 2

2,6-Dimethylanilide of 2-diethylaminomethylbenzoic acid

A solution of 2.37 grams (0.01 mole) of 2-diethylaminomethylbenzoic acid chloride in 50 cc of benzene is treated with 2.42 grams of 2,6-dimethylanilide and the mixture is refluxed on a water bath for four hours. The mixture is filtered from insoluble material, the benzene phase is washed with water and concentrated to dryness. The residue is recrystallized from ligroin Yield: 2.5 grams (80%);

Solid white crystalline, Melting Point: 99°–101° C.

Analysis: Calculated for $C_{20}H_{26}N_2O$: Found: 77.42; H 8.52; N 9.00; Calc.: 77.36; H 8.45; N 9.03.

The other compounds of formula I listed in Table I are prepared by analogous methods.

manifest on the basis of the following work. The data reported hereinbelow relate in every instance to the hydrochloride salts of the individual compounds.

TABLE I

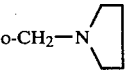

| No | R | —CH₂R' | FORMULA | Melting Point | C% calc. | C% Found | H% calc. | H% Found | N% calc. | N% Found | Melting Point of the HCl Salt |
|---|---|---|---|---|---|---|---|---|---|---|---|
| 1 | CH₃ | o-CH₂NEt₂ | C₂₀H₂₆N₂O | 99–101 | 77.36 | 77.42 | 8.45 | 8.52 | 9.03 | 9.00 | 162–164° |
| 2 | CH₃ | m-CH₂NEt₂ | C₂₀H₂₆N₂O | 100–102 | 77.36 | 77.30 | 8.45 | 8.40 | 9.03 | 9.06 | — |
| 3 | CH₃ | p-CH₂NEt₂ | C₂₀H₂₆N₂O | 141–142 | 77.36 | 77.50 | 8.45 | 8.35 | 9.03 | 9.12 | — |
| 4 | CH₃ | o-CH₂—N(pyrrolidinyl) | C₂₀H₂₄N₂O | 105–108 | 77.87 | 77.67 | 7.85 | 7.80 | 9.09 | 9.06 | 228–230° |
| 5 | CH₃ | m-CH₂—N(pyrrolidinyl) | C₂₀H₂₄N₂O | 120–122 | 77.87 | 77.85 | 7.85 | 7.91 | 9.09 | 9.12 | 230–234° |
| 6 | CH₃ | p-CH₂—N(pyrrolidinyl) | C₂₀H₂₄N₂O | 170–172 | 77.87 | 77.92 | 7.85 | 7.95 | 9.05 | 9.19 | 290–292° |
| 7 | CH₃ | o-CH₂—N(piperidinyl) | C₂₁H₂₆N₂O | 111–114 | 78.81 | 78.62 | 8.13 | 8.06 | 8.69 | 8.75 | 210–212° |
| 8 | CH₃ | m-CH₂—N(piperidinyl) | C₂₁H₂₆N₂O | 118–120 | 78.81 | 78.70 | 8.13 | 8.10 | 8.69 | 8.59 | 252–255° |
| 9 | CH₃ | p-CH₂—N(piperidinyl) | C₂₁H₂₆N₂O | 176–177 | 78.81 | 78.82 | 8.13 | 8.25 | 8.69 | 8.39 | 270–272° |
| 10 | CH₃ | o-CH₂—N(morpholinyl) | C₂₀H₂₄N₂O₂ | 135–138 | 74.03 | 74.05 | 7.46 | 7.42 | 8.64 | 8.61 | 213–216° |
| 11 | CH₃ | m-CH₂—N(morpholinyl) | C₂₀H₂₄N₂O₂ | 108–110 | 74.03 | 74.12 | 7.46 | 7.40 | 8.64 | 8.72 | 172–176° |
| 12 | CH₃ | p-CH₂—N(morpholinyl) | C₂₀H₂₄N₂O₂ | 156–158 | 74.03 | 74.08 | 7.46 | 7.66 | 8.64 | 8.73 | 276–280° |
| 13 | Cl | o-CH₂NEt₂ | C₁₉H₂₃ClN₂O | 89–91 | 62.87 | 62.77 | 6.39 | 6.41 | 7.72 | 7.80 | 209–213° |
| 14 | COOCH₃ | o-CH₂NEt₂ | C₂₁H₂₆N₂O₃ | 79–81 | 71.14 | 71.20 | 7.40 | 7.30 | 7.91 | 7.82 | 183–185° |

The compounds of formula I may be converted by methods well-known in the art into the corresponding salts with pharmaceutically acceptable acids, both inorganic, for instance, hydrochloric acid, hydrobromic acid, sulfuric acid, phosphoric acid, nitric acid, etc., and organic, for instance, citric acid, tartaric acid, malic acid, maleic acid, etc.

As it has been mentioned hereinabove, the compounds according to the present invention exhibit a very high local anaesthetic activity and also anti-arrhythmic activity. The toxicological and pharmacological properties of the compounds of formula I will be

ACUTE TOXICITY

Acute toxicity has been determined in Swiss rats by the intraperitoneal injection of the compounds dissolved in physiological saline solution. The behavior of the animals has then been followed for a period of five days. The $DL_{50}$ has been determined according to the method of I. T. Litchfield and F. Wilcoxon, (J. Pharmacol. Exper. Ther., 96, 99, 1949). The results are reported in Table II, second column. The compound numbers in Table II correspond to the numbers in Table I.

TABLE II

| Compound | DL₅₀ i.p. (mg/kg) | | ANAESTHESIA | | | | Conduction | |
|---|---|---|---|---|---|---|---|---|
| | | | Surface | | Infiltration | | 1/t'max. | |
| | | | $CE_{50}$ | $DL_{50}/CE_{50}$ | $CE_{50}$ | $DL_{50}/CE_{50}$ | (c = 1%) | $DL_{50}/t'$ |
| 1 | 17.2 | (18.3–16.3) | 0.50 | 34 | 0.25 | 69 | 0.33 | 6 |
| 2 | 67.0 | (75.0–59.8) | 0.41 | 163 | 0.23 | 291 | 1.00 | 67 |
| 3 | 82.5 | (87.9–77.4) | 4.78 | 17 | 8.02 | 10 | 0.11 | 9 |
| 4 | 55.0 | (71.1–42.0) | 1.85 | 30 | 0.34 | 162 | 1.00 | 55 |
| 5 | 225 | (249–203) | 24.12 | 9 | 8.01 | 28 | 1.00 | 225 |
| 6 | 215 | (236–195) | 16.03 | 13 | 4.50 | 48 | 0.50 | 107 |
| 7 | 87.1 | (92.5–81.8) | 0.30 | 290 | 0.21 | 414 | 1.00 | 87 |
| 8 | 205 | (226–186) | 2.82 | 73 | 0.36 | 569 | 0.20 | 41 |
| 9 | 210 | (232–190) | 1.92 | 109 | 0.28 | 750 | 0.09 | 19 |
| 10 | 230 | (257–207) | 6.86 | 34 | 2.34 | 98 | 0.09 | 21 |
| 11 | 260 | (284–238) | 11.90 | 22 | 0.95 | 273 | 0.11 | 29 |
| 12 | 230 | (255–208) | 2.82 | 82 | 2.25 | 102 | 0.25 | 57 |
| 13 | 16.3 | (17.6–14.9) | 0.60 | 27 | 0.28 | 58 | 1.00 | 16 |
| 14 | 24.7 | (26.9–22.6) | 0.41 | 60 | 0.43 | 57 | 0.20 | 5 |
| Lidocaine | 142 | (160–131) | 2.30 | 62 | 0.75 | 189 | 0.09 | 13 |

As it is clear from the data in the Table above, a substantial number of the compounds of formula I is substantially less toxic than lidocaine, (α-diethylamino-2,6-dimethyl-acetanilide).

LOCAL ANAESTHESTIC ACTIVITY

The surface anaesthesia has been determined in rabbits according to the method of M. R. A. Change and H. Lobstein (J. Pharmacol. Exper. Ther., 82, 203, 1944). The compounds dissolved in physiological saline solution of pH 7 were injected into the conjunctival sac and the corneal reflux was induced with the brush of Frey six times at intervals of five minutes for a total period of 40 minutes. The extent of surface anaesthesia has been measured quantitatively by measuring the sum of the instances during which the animals did not blink during a period of 40 minutes on 48 possible blinks.

The anaesthesia by infiltration has been determined in guinea pigs according to the method of E. Bulbring and I. Wajda, (Journal of Pharmacol. Exper. Ther. 85, 78, 1945). In each experiment, four doses of the substance in 0.25 cc of physiological saline solution is injected subcutaneously on the back after removal of hair. After five minutes, each animal is punctured six times at intervals of 3–5 minutes.

The test was repeated every five minutes for a period of 30 minutes. The extent of anaesthesia by infiltration was measured quantitatively by determining the sum of the instances in which the animal remained immobile during the thirty minute period on 36 possible blinks.

Anaesthesia by conduction has been determined on frogs according to the method of E. Bulbring and I. Wajda (Journal Pharmacol. Exper. Ther., 85, 78, 1945). The compounds dissolved in physiological saline solution are introduced into the cavity obtained by a transversal incision in the abdomen and separating the viscera in order to expose the lumbar plexus. The period of time necessary to eliminate the reflux of contraction of the lower limbs stimulated by immersion of both posterior legs into hydrochloric acid of increasing concentration between 0.05–0.1–0.2 N for a period not in excess of ten seconds, at intervals of one minute is determined. The extent of anaesthesia of conduction has been determined by measuring the period of time required for each compound in three different concentrations, 0.2%–0.5%–1.0% in order to abolish the reflex of contraction with the concentration of hydrochloric acid indicated hereinabove.

For each compound according to the invention, comparison with lidocaine has been made, the comparison being calculated and expressed as $CE_{50}$, which represents the concentration in percent which permits to achieve 50% of the total responses with respect to the total number of applied stimulating agents in the tests of surface anaesthesia and infiltration anaesthesia. By referring the values of $CE_{50}$ to the values of $DL_{50}$, one obtains a parameter which is analogous to the therapeutic index and which is capable of expressing the correlation between local anaesthetic activity and acute toxicity. This method of evaluation, however, cannot be applied in the case of conduction anaesthesia in frogs because the test does not give quantitative responses since the responses are of the type "everything or nothing." In this latter case, therefore, the parameter of efficacy of each compound is assumed to be the reciprocal of the maximum time at the concentration of 1%. The results are reported in Table II. On the basis of the comparison of the values, $DL_{50}/CE_{50}$ (or $DL_{50}/t$), one notes the clear superiority of some of the compounds of formula I with respect to lidocaine. This superiority is even more clear from an examination of Table III in which the values of toxicity and activity of lidocaine arbitrarily have been made equal to one.

TABLE III

| | | ANAESTHESIA | | | | | |
|---|---|---|---|---|---|---|---|
| | | Surface | | Infiltration | | Conduction | |
| | | | | | | 1/t'max. | |
| Compound | $DL_{50}$ i.p. | Activity * | $DL_{50}/CE_{50}$ | Activity * | $DL_{50}/CE_{50}$ | (c = 1%) with respect to lidocaine | $DL_{50}/t'$ |
| 1 | 0.12 | 4.60 | 0.55 | 3.00 | 0.36 | 3.6 | 0.46 |
| 2 | 0.47 | 5.60 | 2.63 | 3.26 | 1.54 | 11.1 | 5.15 |
| 3 | 0.58 | 0.48 | 0.27 | 0.09 | 0.05 | 1.2 | 0.69 |
| 4 | 0.39 | 1.24 | 0.48 | 2.20 | 0.86 | 11.1 | 4.23 |
| 5 | 1.58 | 0.09 | 0.15 | 0.09 | 0.15 | 11.1 | 17.31 |
| 6 | 1.51 | 0.14 | 0.21 | 0.16 | 0.25 | 5.5 | 8.31 |
| 7 | 0.61 | 7.66 | 4.68 | 3.57 | 2.19 | 11.1 | 6.69 |
| 8 | 1.44 | 0.82 | 1.18 | 2.08 | 3.01 | 2.2 | 3.15 |
| 9 | 1.48 | 1.20 | 1.77 | 2.67 | 3.97 | 1.0 | 1.46 |
| 10 | 1.62 | 0.34 | 0.55 | 0.32 | 0.52 | 1.0 | 1.61 |
| 11 | 1.83 | 0.19 | 0.35 | 0.79 | 1.44 | 1.2 | 2.15 |
| 12 | 1.62 | 0.82 | 1.32 | 0.33 | 0.54 | 2.7 | 4.46 |
| 13 | 0.11 | 3.83 | 0.43 | 2.68 | 0.31 | 11.1 | 1.23 |
| 14 | 0.17 | 5.61 | 1.00 | 1.74 | 0.30 | 2.2 | 0.38 |
| Lidocaine | 1 | 1 | 1 | 1 | 1 | 1 | 1 |

* Activity with respect to lidocaine

ANTI-ARRHYTHMIC ACTIVITY

This determination has been made in Wistar rats, anaesthetized with ethylurethane, (1 g/kg i.p.), according to the method of B. Vargaftig and J. L. Coigner (European Journal Pharmacology, 6, 49, 1969). The compounds dissolved in physiological saline solution, are injected intravenously three minutes prior to the infusion of aconitine, (10 mcg/kg/min.). The extent of anti-arrhythmic activity is determined quantitatively by determining the amount of aconitine necessary to induce ventricular arrhythmia. The data obtained are reported in Table IV. These data show that compounds 1, 13, and 14 are at least twenty times more active than lidocaine and at least ten times more active than quinidine.

TABLE IV

| Compound | mg/kg i.v. | Aconitine i.v. mcg/kg |
|---|---|---|
| 1 | 0.6 | 50 ± 5 |
|  | 1.0 | 67 ± 8 |
|  | 3.0 | 69 ± 8 |
| 2 | 1.0 | 43 ± 8 |
|  | 3.0 | 77 ± 9 |
|  | 6.0 | 82 ± 9 |
| 3 | 1.0 | 38 ± 5 |
|  | 3.0 | 39 ± 6 |
|  | 8.0 | 47 ± 7 |
| 13 | 0.6 | 48 ± 6 |
|  | 1.0 | 65 ± 7 |
|  | 3.0 | 67 ± 7 |
| 14 | 0.6 | 45 ± 8 |
|  | 1.0 | 60 ± 7 |
|  | 3.0 | 81 ± 7 |
| Lidocaine hydrochloride | 12.5 | 41 ± 4 |
|  | 25.0 | 54 ± 5 |
| Quinidine sulfate | 10.0 | 50 ± 3 |
|  | 40.0 | 88 ± 11 |

The compounds of the present invention exhibit anti-arrhythmic properties and local anaesthestic properties with a mechanism of action similar to mexiletine and tocainide which reduce the number of channels for sodium because they particularly influence the rapid response and the slow sodium-dependent response, (O. Hauswirth and B. H. Singh: Pharmacology Review, 30, 5, 1978).

In clinical trial, preliminary tests have shown the superior anaesthestic activity and anti-arrhythmic activity with respect to lidocaine of the compounds according to the present invention which exhibit greater activity and which are more tolerated in the pharmacological tests reported hereinabove when the compounds are used in adequate formulations as indicated hereinbelow.

The following typical formulations are described hereinbelow for the purpose of illustrating the present invention.

FORMULATIONS FOR PARENTERAL ADMINISTRATION (a) For use as a local anaesthetic:

Vials of 2 cc capacity are filled with a sterile aqueous solution of the compounds according to the present invention in a 1–2% concentration, with or without an epinephrine or norepinephrine in the ratio of 1:80,000 or 1:50,000 together with 0.1% sodium metabisulfite, (for conditions of the oral cavity, tongue, teeth, etc.).

Vials of 2,5,10,20 cc capacity and bottles containing aqueous sterile solutions of the compounds according to the present invention in the concentration of 0.25%–5% with or without epinephrine in the ratio of 1:20,000 or 1:100,000, together with 0.1% sodium metabisulfite, (for anaesthesia by infiltration or conduction, regional block, epidural and caudal, etc.)

(b) For use as an anti-arrhythmic agent:

Vials of 2,5,10 cc capacity and bottles of 50 cc capacity are used containing aqueous sterile solutions of the compounds according to the present invention in the concentration of 0.5%–10% (by the endovenous and intramuscular route).

FORMULATIONS FOR TOPICAL USE

These formulations contain the compounds according to the present invention in the concentration of 1%–5% with or without an antiseptic and are provided in the form of:

A gel, with excipients for instance, sodium carboxymethylcellulose or carboxypolymethylene with triethanolamine and water (for endoscopic handling).

A cream (for instance used with excipients such as cetyltrimethylammonium bromide, cetyl alcohol, white wax, sodium lauryl sulfate, glycerine, and water). These creams are particularly suitable in cases of burns, erythema due to the sun rays, rashes, anogenital itching, and insect bites.

Hydrophilic ointment (with excipients such as polyglycols, stearyl alcohol, sodium laurylsulfate, glycerine, water). These ointments are used in the case of burns, erythema caused by sun rays, rashes, anogenital itching, or insect bites.

Viscous solutions, (The excipients may be sodium carboxymethylcellulose in water). These solutions are suitable in case of irritation and inflammation of the oral cavity and the pharynx.

Sprays, (The excipients may be for instance, menthol, cineole, propylene glycol, together with propellants) for broncoscopic use.

Collyrium, (The excipients may be methylcellulose in water) for corneal anaesthesia without mydriasis.

Suppositories (The excipients may be triglycerides of fatty acids or polyethylene glycols to be used in case of hemorrhoids, anal itching, anal and rectum conditions, and tenesmus).

What is claimed is:

1. A benzamide of formula I

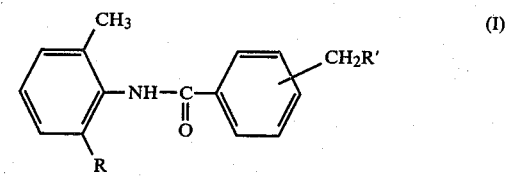

wherein
R = CH$_3$, Cl or COOCH$_3$;
R' is a member selected from the group of dialkylamine, pyrrolidine, piperidine, and morpholine radicals,
CH$_2$R' is in position ortho, meta, or para with respect to the carbonyl group;
and salts thereof with a pharmaceutically acceptable acid.

2. A compound according to claim 1 which is the 2,6-dimethylanilide of 2-diethylaminomethylbenzoic acid and a pharmaceutically acceptable salt thereof.

3. A compound according to claim 1 which is the 2,6-dimethylanilide of 3-diethylaminomethylbenzoic acid, and a pharmaceutically acceptable salt thereof.

4. A compound according to claim 1 which is the 2,6-dimethylanilide of 4-diethylaminomethylbenzoic acid and a pharmaceutically acceptable salt thereof.

5. A compound according to claim 1 which is the 2,6-dimethylanilide of 2-pyrrolidinomethylbenzoic acid and a pharmaceutically acceptable salt thereof.

6. A compound according to claim 1 which is the 2,6-dimethylanilide of 3-pyrrolidinomethyl-benzoic acid and a pharmaceutically acceptable salt thereof.

7. A compound according to claim 1 which is the 2,6-dimethylanilide of 4-pyrrolidinomethyl-benzoic acid, and a pharmaceutically acceptable salt thereof.

8. A compound according to claim 1 which is the 2,6-dimethylanilide of 2-piperidinomethyl-benzoic acid and a pharmaceutically acceptable salt thereof.

9. A compound according to claim 1 which is the 2,6-dimethylanilide of 3-piperidinomethyl-benzoic acid and a pharmaceutically acceptable salt thereof.

10. A compound according to claim 1 which is the 2,6-dimethylanilide of 4-piperidinomethyl-benzoic acid, and a pharmaceutically acceptable salt thereof.

11. A compound according to claim 1 which is the 2,6-dimethylanilide of 2-morpholinomethyl-benzoic acid and a pharmaceutically acceptable salt thereof.

12. A compound according to claim 1 which is the 2,6-dimethylanilide of 3-morpholinomethyl benzoic acid, and a pharmaceutically acceptable salt thereof.

13. A compound according to claim 1 which is the 2,6-dimethylanilide of 4-morpholinomethyl benzoic acid, and a pharmaceutically acceptable salt thereof.

14. A compound according to claim 1 which is the 2-chloro-6-methylanilide of 2-diethylaminomethyl-benzoic acid, and a pharmaceutically acceptable salt thereof.

15. A compound according to claim 1 which is 2-carbomethoxy-6-methylanilide of 2-diethylaminomethyl-benzoic acid and a pharmaceutically acceptable salt thereof.

16. A pharmaceutical composition exhibiting local anaesthestic or anti-arrhythmic activity in unit dosage form which contains an effective amount of a compound according to claim 1 or a pharmaceutically acceptable salt thereof and a pharmaceutically acceptable carrier.

* * * * *